United States Patent
Pappas, III et al.

(10) Patent No.: US 7,614,938 B1
(45) Date of Patent: Nov. 10, 2009

(54) RECONDITIONED MEDICAL DEVICES

(76) Inventors: John C. Pappas, III, 17 Southwood Dr., Southborough, MA (US) 01772; Paul N. Pappas, 18 Nicholas Cir., Marlborough, MA (US) 01752

( * ) Notice: Subject to any disclaimer, the term of this patent is extended or adjusted under 35 U.S.C. 154(b) by 424 days.

(21) Appl. No.: 11/276,291

(22) Filed: Feb. 22, 2006

Related U.S. Application Data

(60) Provisional application No. 60/655,042, filed on Feb. 22, 2005.

(51) Int. Cl.
*B24B 1/00* (2006.01)

(52) U.S. Cl. .............................. 451/45; 451/53; 451/54; 451/56; 451/443; 76/119; 606/80; 606/85; 30/346.54; 30/350

(58) Field of Classification Search .................... 451/28, 451/38, 45, 53, 54, 56, 443; 76/24.1, 104.1, 76/119; 606/45, 79, 80, 82–85; 30/346.53, 30/346.54, 350
See application file for complete search history.

(56) References Cited

U.S. PATENT DOCUMENTS

| | | | |
|---|---|---|---|
| 4,625,725 A | 12/1986 | Davison et al. | |
| 4,770,067 A | 9/1988 | Liu et al. | |
| 5,733,664 A | 3/1998 | Kelley et al. | |
| 5,791,968 A * | 8/1998 | Matsumura et al. | 451/5 |
| 2001/0029386 A1 | 10/2001 | Matsunani et al. | |
| 2003/0017015 A1 * | 1/2003 | Strubler | 408/230 |
| 2005/0228372 A1 * | 10/2005 | Truckai et al. | 606/41 |

OTHER PUBLICATIONS

Precision Diamond Ground Tungsten Carbide Inserts for Needle Holding and Surgical Instruments [online], Circa Dec. 4, 2000 [retrieved on Feb. 21, 2005] Retrieved from Internet Archive <http://web.archive.org/web/20000120415280/http://www.abrasive-form.com/car.htm>.

Nickel Carbide [online], Circa Aug. 3, 2001, [retrieved on Feb. 21, 2005] Retrieved from Internet Archive <http://web.archive.org/web/20010803122258/http://texasball.com/NICHELCARBIDE.htm>.

* cited by examiner

*Primary Examiner*—Eileen P. Morgan
(74) *Attorney, Agent, or Firm*—Scott E. Kamholz; Foley Hoag LLP

(57) ABSTRACT

A method of reconditioning a medical device may include removing a portion of the medical device, and attaching to the medical device a replacement piece formed from nickel carbide and sized, shaped, and positioned to replace the portion removed.

25 Claims, 2 Drawing Sheets

RECONDITIONED MEDICAL DEVICES

CROSS-REFERENCE TO RELATED APPLICATION

This application claims the benefit of U.S. Provisional Application No. 60/655,042, filed Feb. 22, 2005, which is hereby incorporated herein by this reference.

BACKGROUND

Medical devices that are designed for repeated use typically become worn with time and eventually must be reconditioned or discarded. Devices with dulled cutting edges may be sharpened or otherwise treated to extend their useful lives. Such sharpening involves the removal of material from the cutting edge so that a new cutting edge can be formed. This can be done a limited number of times, involves expense, consumes time during which the device is unavailable for use, and may result in a device with changed properties.

SUMMARY

The application discloses reconditioned medical devices and methods for making them. In one embodiment, a method of reconditioning a medical device includes removing a portion of the medical device and attaching to the medical device a replacement piece formed from nickel carbide. The replacement piece may be sized, shaped, and positioned to replace the portion removed.

BRIEF DESCRIPTION OF THE DRAWINGS

Arrows between steps are not meant to indicate a particular temporal order to steps. Rather, they are provided to show that a group of steps are associated in one process. Steps may occur in any order. Steps bordered by bracketed arrows "(→)" are optional steps and may occur anywhere in a process.

DETAILED DESCRIPTION

The need for reconditioning medical devices can be reduced or eliminated by making devices from materials more durable than those typically used. Surgical tools made from nickel carbide, for example, are described in U.S. Provisional Application Ser. No. 60/404,513, filed Aug. 19, 2002, and in PCT Application Ser. No. PCT/US2003/025903 (WO 2004/016290), filed Aug. 19, 2003, both of which are hereby incorporated herein by this reference.

Although a device can be newly manufactured from more durable materials, it may not be necessary to form the entire device from a special material, especially when only one portion of the device is subjected to wear. For example, the cutting edge of a cutting tool is subjected to considerably more wear than other portions of the device, so a medical device can be reconditioned by removing the cutting edge and replacing with a new cutting edge. This can be done with a used device as well as with an unused device. When so modifying an unused device, the process may be thought of as "customization," but the term "reconditioned" as used in this disclosure includes modification of either used or unused devices.

Figure 1:
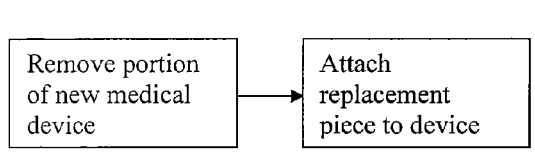
FIG. 1 depicts an exemplary method for reconditioning medical devices.

FIG. 1 illustrates the basic method. At it simplest, the method involves removing a portion of a medical device and replacing it with a replacement piece. The piece to be removed can be removed in a wide variety of ways, such as grinding, sawing, snapping, melting, etc.

Figure 2:
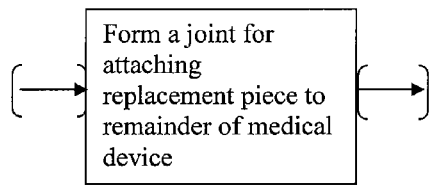
FIGS. 2, 3, and 4 depict portions of exemplary methods for reconditioning medical devices.
Figure 5:
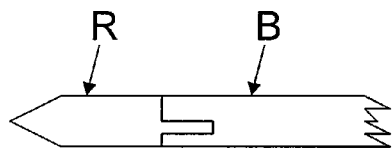
FIGS. 5, 6, 6A, 7, and 7A depict exemplary joints for joining a replacement piece to a medical device.
Figure 6:
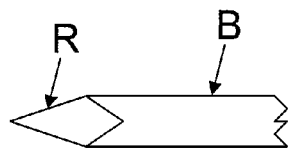
Figure 7:
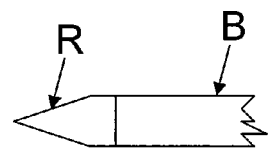
Figure 7A:
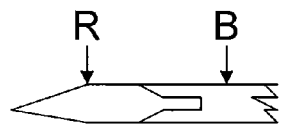

As shown in FIG. 2, a joint can be formed to attach the replacement piece to the medical device. A wide variety of joints may be employed, such as tongue-and-groove joints (FIG. 5), v-joints (FIGS. 6 and 6A), butt joints (FIG. 7), and combined v-tongue joints (FIG. 7A) to join a replacement piece R to body B of a medical device. The device portion of the joint can be formed when the device is initially "decapitated" by so selecting the shape of the piece to be removed as to leave the appropriately-shaped surface. Alternatively, the device portion of the joint can be formed by removing or adding material to the already-blunted device to form the mating surface. For example, the blunted device can be ground to create the joint surface.

When the corresponding joint surfaces are prepared, the two pieces may be joined by a variety of methods suitable for the particular materials being joined, such as blending, brazing, and/or soldering.

Figure 6A:
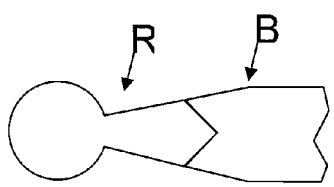

FIG. 6A shows a schematic view of an abrader (such as used in arthroscopic or endoscopic procedures) in which the ball tip (having cutting grooves that are not shown) is replaced by replacement tip R and joined by a v-joint to abrader shaft B. The abrader replacement tip may be joined to the shaft using the joints described herein.

The replacement piece can be made by a variety of materials. Of particular interest are carbides for their desirable qualities of strength, hardness, and density. Tungsten carbides, and especially nickel binder tungsten carbides, may be particularly well suited for use in replacement cutting edges for surgical instruments. Examples of devices that can be reconditioned by the techniques described herein include a chisel, an osteotome, a rasp, a dual rasp, a rongeur, a microrongeur, a pituitary rongeur, a Kerrison rongeur, an abrader, a curette, a file, a gouge, a punch, a meniscus knife, a reamer, a resection knife, a scalpel, a clamp, a needle driver, a grasper, a speculum, a dilator, and a scissors. Carbides are discussed in greater detail in the patent applications cited above.

Figure 9:
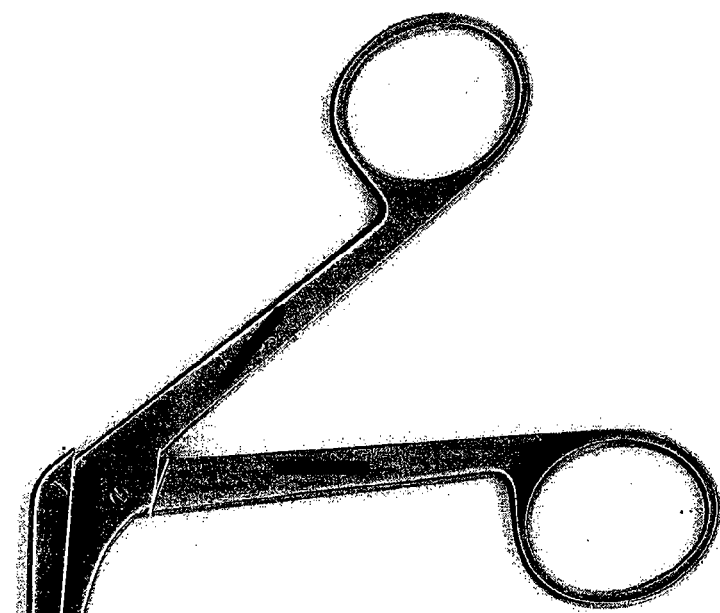
FIG. 9 depicts an exemplary device having apposed surfaces.
Figure 10:
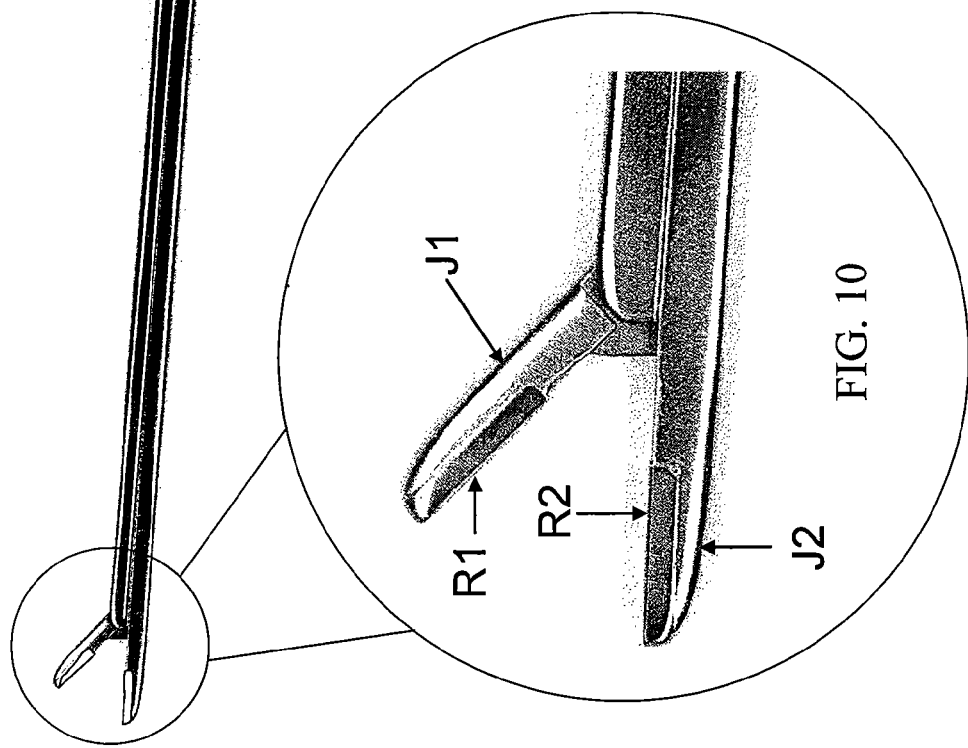
FIG. 10 provides a magnified view of a portion of FIG. 9.

If a device to be reconditioned has more than one surface expected to contact a subject, then the additional surfaces may be reconditioned. In particular, when a device has apposed surfaces (such as the jaws of a rongeur or a clamp, etc., FIG. 9), portions at both surfaces may be removed and replaced as described herein. As shown in FIG. 10, replacement surfaces R1 and R2 have been attached to jaws J1 and J2, respectively, of a device having apposed surfaces. If it is desired that the reconditioned device preserve the original relationship between the apposed surfaces (i.e., same clearance, angle, "bite," etc.), then the replacement piece should have approximately, preferably near identically, the same size and shape as the removed portion. If it is not important to preserve the original dimensions, then the replacement piece need not be the same size and/or shape as the removed portion.

Figure 3:
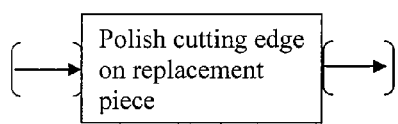

When the medical device being refurbished is one that is expected to be placed in contact with more than one patient (that is, used with one patient, then cleaned, and then used with another patient), dangers associated with re-use, particularly patient-to-patient transmission of infective particles, can be minimized by treating the contact surfaces so that they tend to exclude pathogens. This can be done, for example, by giving the contact surface so low a porosity that infective particles cannot efficiently adhere or can be easily removed using standard sterilizing or cleaning techniques such as washing, autoclaving, etc. A variety ways to give such a low-porosity finish are disclosed in U.S. Provisional Application Ser. No. 60/404,513, filed Aug. 19, 2002, and in PCT Application Ser. No. PCT/US2003/025903 (WO 2004/016290), filed Aug. 19, 2003, as are particular porosity ranges that are particularly effective for preventing transmission of prions. Briefly, techniques include polishing (FIG. 3), hot isostatic pressing, and forming the cutting edge with fine grade carbide particles.

Figure 4:
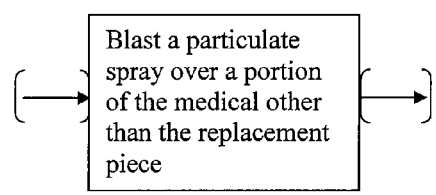
Figure 8:
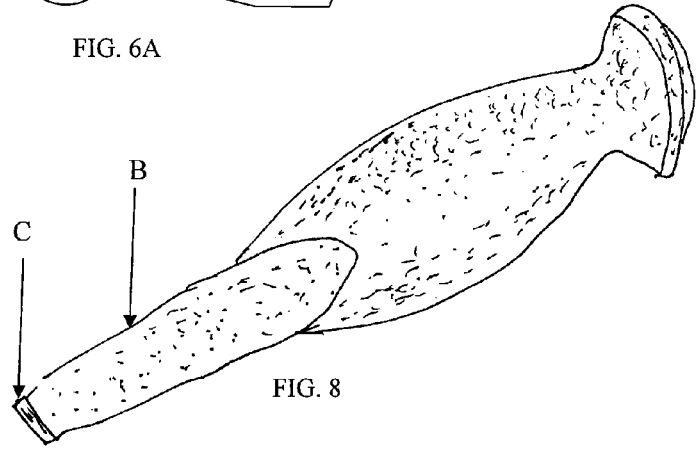
FIG. 8 depicts an exemplary medical device having a satin finish.

The body portion of a medical device can be processed to give it a fine satin-like finish. The body may be blasted with a particulate spray (FIG. 4), such as a spray of aluminum oxide beads, glass beads, or a mixture thereof. Other sprays, such as crushed glass, blasting garnet, silicon carbide, and/or walnut shells may be used. FIG. 8 shows a sketch of an exemplary Smith Peterson osteotome with the blasting treatment. The stippled region (on the main body B of the medical device) indicates the fine satin finish, while the cutting edge C of the osteotome has a shiny, mirror-like finish. This treatment can provide both functional and ornamental advantages: the satin finish can make the body of the medical device less slippery and therefore easier to handle. It may also give the device an aesthetically-pleasing appearance.

These and other features are described in the following claims.

The invention claimed is:

1. A method of reconditioning a medical device, comprising:
   removing a portion of the medical device, the removed portion comprising a cutting edge;
   attaching to the medical device a replacement piece formed from nickel carbide, comprising a replacement cutting edge, and sized, shaped, and positioned to replace the portion removed; and
   treating a surface of the replacement cutting edge so that the replacement cutting edge surface has no more than about 10 pores per square centimeter larger than about 15 nanometers in size.

2. The method of claim 1, wherein treating comprises polishing the replacement cutting edge surface.

3. The method of claim 2, wherein the replacement cutting edge surface is polished so that it has no more than about 10 pores per square centimeter larger than about 12 nanometers in size.

4. The method of claim 3, wherein the replacement cutting edge surface is polished so that it has no more than about 10 pores per square centimeter larger than about 10 nanometers in diameter.

5. The method of claim 3, wherein the replacement cutting edge surface is polished so that it has no more than about 10 pores per square centimeter larger than about nanometers in diameter.

6. The method of claim 1, wherein the nickel carbide has a density of about 14 to about 17 g/cm$^3$.

7. The method of claim 6, wherein the nickel carbide has a density of about 14 to about 15 g/cm$^3$.

8. The method of claim 1, wherein the nickel carbide comprises about 88.5 percent tungsten carbide and about 11.5 percent nickel alloy binder.

9. The method of claim 1, wherein the medical device comprises a surgical tool.

10. The method of claim 9, wherein the surgical tool comprises at least one of a chisel, an abrader, an osteotome, a rasp, a dual rasp, a rongeur, a microrongeur, a pituitary rongeur, a Kerrison rongeur, a curette, a file, a gouge, a punch, a meniscus knife, a reamer, a resection knife, a scalpel, a clamp, a needle driver, a grasper, and a scissors.

11. The method of claim 9, wherein the surgical tool comprises at least one of a chisel, an abrader, an osteotome, a rasp, a rongeur, a curette, a file, a gauge, a meniscus knife, a reamer, a resection knife, and a scalpel.

12. The method of claim 9, wherein the surgical tool comprises an osteotome.

13. The method of claim 9, wherein the surgical tool comprises a chisel.

14. The method of claim 9, wherein the surgical tool comprises a rasp.

15. The method of claim 9, wherein the surgical tool comprises a rongeur.

16. The method of claim 9, wherein the surgical tool comprises an abrader.

17. The method of claim 1, wherein removing comprises cutting off the portion to be removed.

18. The method of claim 1, wherein attaching comprises brazing.

19. The method of claim 1, wherein attaching comprises forming a joint between the remaining portion of the medical device and the replacement piece.

20. The method of claim 19, wherein the joint is a butt joint, a tongue-and-groove joint, or a v-joint.

21. The method of claim 1, wherein the medical device is pre-used.

22. The method of claim 1, further comprising blasting a particulate spray over a portion of the medical other than the replacement piece.

23. A reconditioned medical device made according to the method of claim 1.

24. The method of claim 1, wherein treating comprises hot isostatic pressing.

25. The method of claim 1, wherein treating comprises forming the replacement cutting edge surface with fine grade carbide particles.

* * * * *

UNITED STATES PATENT AND TRADEMARK OFFICE
CERTIFICATE OF CORRECTION

| | |
|---|---|
| PATENT NO. | : 7,614,938 B1 |
| APPLICATION NO. | : 11/276291 |
| DATED | : November 10, 2009 |
| INVENTOR(S) | : Pappas, III et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 685 days.

Signed and Sealed this

Nineteenth Day of October, 2010

David J. Kappos
*Director of the United States Patent and Trademark Office*